United States Patent
Watanabe et al.

(10) Patent No.: US 9,475,032 B2
(45) Date of Patent: Oct. 25, 2016

(54) MOLDED ARTICLE FOR HYDROCARBON ADSORPTION

(71) Applicant: SHOWA DENKO K.K., Tokyo (JP)

(72) Inventors: Yoshihiro Watanabe, Oita (JP); Keisuke Kishida, Oita (JP); Yoshikuni Okumura, Oita (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

(21) Appl. No.: 14/906,818

(22) PCT Filed: Jul. 1, 2014

(86) PCT No.: PCT/JP2014/067520
§ 371 (c)(1),
(2) Date: Jan. 21, 2016

(87) PCT Pub. No.: WO2015/012068
PCT Pub. Date: Jan. 29, 2015

(65) Prior Publication Data
US 2016/0175810 A1    Jun. 23, 2016

(30) Foreign Application Priority Data

Jul. 26, 2013 (JP) .................... 2013-155607

(51) Int. Cl.
| | | |
|---|---|---|
| *B01J 38/68* | (2006.01) | |
| *B01J 20/22* | (2006.01) | |
| *C07C 7/12* | (2006.01) | |
| *C07F 1/08* | (2006.01) | |
| *C07F 3/06* | (2006.01) | |
| *B01D 53/02* | (2006.01) | |
| *B01J 20/28* | (2006.01) | |
| *B01J 20/30* | (2006.01) | |
| *B01J 20/26* | (2006.01) | |

(52) U.S. Cl.
CPC ............ *B01J 20/223* (2013.01); *B01D 53/02* (2013.01); *B01J 20/226* (2013.01); *B01J 20/261* (2013.01); *B01J 20/2803* (2013.01); *B01J 20/3007* (2013.01); *C07C 7/12* (2013.01); *C07F 1/08* (2013.01); *C07F 3/06* (2013.01); *B01D 2253/1122* (2013.01); *B01D 2253/20* (2013.01); *B01D 2257/7022* (2013.01)

(58) Field of Classification Search
CPC ........................................................ B01J 38/68
USPC ............................................................. 502/24
See application file for complete search history.

(56) References Cited

U.S. PATENT DOCUMENTS

| | | |
|---|---|---|
| 2003/0222023 A1 | 12/2003 | Mueller et al. |
| 2006/0099398 A1 | 5/2006 | Hesse et al. |
| 2014/0224120 A1 | 8/2014 | Inubushi et al. |

FOREIGN PATENT DOCUMENTS

| | | |
|---|---|---|
| JP | 2005-528204 A | 9/2005 |
| JP | 2006-297278 A | 11/2006 |
| JP | 2008-518781 A | 6/2008 |
| JP | 2009-208028 A | 9/2009 |
| JP | 2010-058034 A | 3/2010 |
| JP | 2010-149476 A | 7/2010 |
| JP | 2010-158617 A | 7/2010 |
| JP | 2011-067783 A | 4/2011 |
| JP | 2011-231210 A | 11/2011 |
| JP | 2013-107826 A | 6/2013 |
| WO | 2013/035702 A1 | 3/2013 |

OTHER PUBLICATIONS

Kazuhiro Uemura et al., Expected Materials for the Future, 2002, pp. 44-51, vol. 2, No. 12.
International Search Report of PCT/JP2014/067520 dated Sep. 30, 2014.

*Primary Examiner* — Edward Johnson
(74) *Attorney, Agent, or Firm* — Sughrue Mion, PLLC (57) ABSTRACT

Provided is a molded article for hydrocarbon adsorption, in which a porous metal complex, the structure of which may vary with adsorption and desorption of gases, can exhibit to a sufficient degree the adsorption and desorption capabilities inherent to the complex. This molded article for hydrocarbon adsorption is characterized by including (A) a metal complex constituted by metal ions, and organic ligands capable of bonding to the metal ions, and (B) a polymer binder component containing within its molecules a total of 0.3 mmol/g to 8.0 mmol/g, inclusive, of at least one functional group selected from group consisting of the carboxyl group, the hydroxyl group, amino groups, the mercapto group, epoxy groups, and the sulfo group.

14 Claims, 5 Drawing Sheets

ND STAGE OF INTERNATIONAL

MOLDED ARTICLE FOR HYDROCARBON ADSORPTION

CROSS REFERENCE TO RELATED APPLICATIONS

This application is a National Stage of International Application No. PCT/JP2014/067520 filed Jul. 1, 2014, claiming priority based on Japanese Patent Application No. 2013-155607 filed Jul. 26, 2013, the contents of all of which are incorporated herein by reference.

TECHNICAL FIELD

The present invention relates to an adsorbent molded article that can be used as an adsorbent, storage material or separating material for a hydrocarbon, and more particularly, to the shaping of a porous metal complex that can adsorb adsorbates as an adsorbent, storage material or separating material.

BACKGROUND ART

Porous metal complexes that are useful for separating a specific gas from a mixed gas have been developed. For example, Patent Document 1 describes a porous metal complex in which the characteristics of both a gate-type polymer complex exhibiting open-gate type gas adsorption and an type-I complex exhibiting type-I gas adsorption are changed by a switching material. In addition, Patent Document 2 and Patent Document 3 describe a porous metal complex that only selectively adsorbs a specific gas accompanying a change in pore structure or size. Moreover, Patent Document 3 and Non-Patent Document 1 describe a flexible porous metal complex, which changes its structure depending on the type of gas contacted thereby, and a gas separation method using that porous metal complex. The term "porous" described herein refers to a metal complex having a special structure at the molecular level (voids) of a size that can accommodate and release hydrocarbon molecules as target adsorbates. In the case of a metal complex having a flexible structure, the shape and/or size of voids may change due to a structural change caused by pressure or other external stimulus.

However, these documents do not specifically describe the form of a porous metal complex in the case of using in an actual industrial separation process. In addition, although Patent Document 4 describes a molded article composed of a porous metal complex and a binder, the binder is an inorganic compound and there is no description relating to the effects of the binder on the adsorption and desorption behavior of the molded article.

PRIOR ART DOCUMENTS

Patent Documents

[Patent Document 1] Japanese Unexamined Patent Publication No. 2010-058034
[Patent Document 2] Japanese Unexamined Patent Publication No. 2009-208028
[Patent Document 3] Japanese Unexamined Patent Publication No. 2010-158617
[Patent Document 4] Japanese Translation of PCT International Application Publication No. 2008-518781

Non-Patent Documents

[Non-Patent Document 1] Kazuhiro Uemura and Susumu Kitagawa: Future Materials, Vol. 2, pp. 44-51 (2002)

SUMMARY OF THE INVENTION

Problems to be Solved by the Invention

In the case of using, for example, zeolite or a molecular sieve as an adsorbent for pressure swing adsorption in an actual industrial production process, the adsorbent powder is typically used after molding into pellets in order to facilitate handling. Pellets are molded by compressing and molding the adsorbent powder using a tableting machine and the like. However, in the case of pelletizing a porous metal complex having a flexible structure, such that the structure thereof changes accompanying gas adsorption in the manner of a porous metal complex as previously described, by tableting using an ordinary binder resin, adsorption performance may decrease if the porous metal complex is molded into a tablet under high pressure so as to give the molded article adequate strength or if the powder is molded by adding a large amount of binder. On the other hand, if the powder is molded into a tablet under low pressure so as to prevent a decrease in adsorption performance or the amount of binder is reduced, this causes problems, such as insufficient crushing strength and disintegration and pulverization of the molded article as a result of being unable to accommodate a structural change accompanying adsorption and desorption.

With the foregoing in view, an object of the present invention is to provide an adsorbent molded article capable of adequately demonstrating the inherent adsorption-desorption performance of a porous metal complex that undergoes a structural change due to the gas adsorption and desorption.

Means for Solving the Problems

As a result of conducting extensive studies to solve the aforementioned problems, the inventors of the present invention have found that, by mixing a polymer binder component (B), containing at least one functional group selected from the group consisting of a carboxyl group, hydroxyl group, amino group, mercapto group, epoxy group and sulfo group ($-SO_2OH$) at a total of 0.3 mmol/g to 8.0 mmol/g in a molecule thereof, with a metal complex (A) and molding into a molded article, the molded article can accommodate structural changes of the porous metal complex attributable to gas absorption and desorption, and the resulting molded article can adequately demonstrate the superior adsorption-desorption performance of the metal complex (A), thereby leading to completion of the present invention. Namely, the present invention relates to [1] to [14] indicated below.

[1] A molded article for hydrocarbon adsorption comprising a metal complex (A), composed of metal ions and organic ligands capable of bonding with the metal ions; and a polymer binder component (B), which contains at least one functional group selected from the group consisting of a carboxyl group, hydroxyl group, amino group, mercapto group, epoxy group and sulfo group at a total of 0.3 mmol/g to 8.0 mmol/g in a molecule thereof.

[2] The molded article for hydrocarbon adsorption described in [1], wherein a functional group of the polymer binder component (B) is a hydroxyl group or carboxyl group.

[3] The molded article for hydrocarbon adsorption described in [1] or [2], wherein the polymer binder component (B) is an ethylenic hydrocarbon polymer, polyester, polyamide or polyether.

[4] The molded article for hydrocarbon adsorption described in any of [1] to [3], wherein the polymer binder component (B) is a copolymer of a (meth)acrylic acid ester having 1 to 10 carbon atoms and (meth)acrylic acid.

[5] The molded article for hydrocarbon adsorption described in any of [1] to [4], which contains 50% by weight to 97% by weight of the metal complex (A).

[6] The molded article for hydrocarbon adsorption described in any of [1] to [5], wherein the organic ligands are at least one organic compound selected from the group consisting of the following (1) to (3):

organic ligand (1): an organic compound having two or more carboxyl groups and/or hydroxyl groups, not having a heterocyclic ring, and capable of bidentate coordination with the metal ions;

organic ligand (2): a saturated or unsaturated, monocyclic or polycyclic heterocyclic compound having a carboxyl group or hydroxyl group, having one heteroatom selected from N, O or S in a ring thereof, and capable of bidentate coordination with the metal ions; and organic ligand (3): a saturated or unsaturated, monocyclic or polycyclic heterocyclic compound having two or more heteroatoms selected from the group consisting of N, O and S in one or a plurality of rings thereof, and capable of bidentate coordination with the metal ions.

[7] The molded article for hydrocarbon adsorption described in [6], wherein the organic ligand (1) is at least one type selected from the group consisting of an alkylene dicarboxylic acid compound having 4 to 20 carbon atoms, an alkenylene dicarboxylic acid compound having 4 to 20 carbon atoms, a dicarboxylic acid compound represented by the following general formulas (I) to (IV), and a hydroxy-carboxylic acid compound represented by the following general formula (V):

wherein $R^1$ respectively and independently represents a hydrogen atom, halogen atom, alkyl group having 1 to 4 carbon atoms, alkoxy group having 1 to 4 carbon atoms, formyl group, acyloxy group having 1 to 4 carbon atoms, alkoxycarbonyl group having an alkoxy group having 1 to 4 carbon atoms, nitro group, cyano group, carboxyl group, amino group, monoalkylamino group having 1 to 4 carbon atoms, dialkylamino group having an alkyl group having 1 to 4 carbon atoms or acylamino group having 1 to 4 carbon atoms, and two or more of $R^2$ may condense to form a ring;

wherein $R^2$ respectively and independently represents a hydrogen atom, halogen atom or alkyl group having 1 to 4 carbon atoms, X represents a hydrogen atom, alkyl group having 1 to 4 carbon atoms, alkenyl group having 2 to 4 carbon atoms, alkynyl group having 2 to 4 carbon atoms, alkoxy group having 1 to 4 carbon atoms, nitro group, carboxyl group, hydroxyl group or amino group; and wherein $R^3$ respectively and independently represents a hydrogen atom, alkyl group having 1 to 4 carbon atoms, alkenyl group having 2 to 4 carbon atoms, alkynyl group having 2 to 4 carbon atoms or alkoxy group having 1 to 4 carbon atoms.

[8] The molded article for hydrocarbon adsorption described in [6], wherein the organic ligand (2) is at least one type selected from the group consisting of compounds represented by the following general formulas (VI) to (VIII):

-continued (VIII)

wherein R³ respectively and independently represents a hydrogen atom, alkyl group having 1 to 4 carbon atoms, alkenyl group having 2 to 4 carbon atoms, alkynyl group having 2 to 4 carbon atoms or alkoxy group having 1 to 4 carbon atoms.

[9] The molded article for hydrocarbon adsorption described in [6], wherein the organic ligand (3) is at least one type selected from the group consisting of compounds represented by the following general formulas (IX) to (XII):

(IX)

(X)

(XI)

(XII)

wherein Y represents an oxygen atom, sulfur atom, —CH₂—, —CH(OH)—, —CO—, —NH—, —C₂N₄—, —C≡C—, —C₂H₂— or —C₆H₄—, R⁴ respectively and independently represents a hydrogen atom, halogen atom, alkyl group having 1 to 4 carbon atoms, alkoxy group having 1 to 4 carbon atoms, formyl group, acyloxy group having 1 to 4 carbon atoms, alkoxycarbonyl group having an alkoxy group having 1 to 4 carbon atoms, nitro group, cyano group, carboxyl group, amino group, monoalkylamino group having 1 to 4 carbon atoms, dialkylamino group having an alkyl group having 1 to 4 carbon atoms or acylamino group having 1 to 4 carbon atoms, and n is an integer of 0 to 3.

[10] The molded article for hydrocarbon adsorption described in any of [1] to [9], wherein the metal ions are a copper ion or zinc ion.

[11] The molded article for hydrocarbon adsorption described in any of [1] to [10], wherein the hydrocarbon targeted for adsorption is a hydrocarbon having 2 to 5 carbon atoms.

[12] The molded article for hydrocarbon adsorption described in [11], wherein the hydrocarbon having 2 to 5 carbon atoms is 1,3-butadiene.

[13] The molded article for hydrocarbon adsorption described in any of [1] to [12], which is produced by a tableting method.

[14] A method for producing a molded article for hydrocarbon adsorption, comprising annealing the molded article described in any of [1] to [13] obtained by tableting at a temperature equal to or higher than the glass transition temperature (Tg) of the polymer binder (B).

Effects of the Invention

The molded article for hydrocarbon adsorption of the present invention is a molded article that does not significantly impair the inherent adsorption performance of the porous metal complex (A). In addition, the molded article for hydrocarbon adsorption of the present invention can easily recover its adsorption performance by placing it in a reduced pressure environment. Thus, the molded article for hydrocarbon adsorption of the present invention can be used as an adsorbent, storage material or separating material depending on the purpose of use.

MODE FOR CARRYING OUT THE INVENTION

Although the following provides a detailed explanation of the present invention, the following description should not be interpreted as disclosing all embodiments of the present invention or all advantages relating to the present invention.

1. Molded Article for Hydrocarbon Adsorption

The molded article for hydrocarbon adsorption of the present invention comprises a porous metal complex (A), having a porous structure composed of metal ions and organic ligands capable of bonding with the metal ions, and a polymer binder component (B), which contains at least one functional group selected from the group consisting of a carboxyl group, hydroxyl group, amino group, mercapto group, epoxy group and sulfo group at a total of 0.3 mmol/g to 8.0 mmol/g in a molecule thereof. A preferable hydrocarbon (gas) targeted for adsorption is a hydrocarbon having 2 to 5 carbon atoms, such as ethane, ethylene, acetylene, propane, propylene, methylacetylene, n-butane, isobutane, 1-butene, trans-2-butene, isobutene, 1,3-butadiene, 3-methyl-1-butene, isopentane, 1-pentene, 2-methyl-1-butene, n-pentane, trans-2-pentene, isoprene and piperylene. Among these hydrocarbons, 1,3-butadiene is particularly preferable.

2. Metal Complex (A)

The metal complex (A) contained in the molded article for hydrocarbon adsorption of the present invention has a porous structure formed from metal ions and organic ligands capable of bonding with the metal ions. This porous structure contains pores at the molecular level, and can contain gas molecules within those pores.

The metal complex preferably has a flexible structure such that the aforementioned pores can selectively adsorb a specific type of gas accompanying a change in the structure or size thereof induced by an external stimulus, such as pressure. These pores can selectively adsorb a specific type of gas. Thus, the metal complex (A), according to the present invention, can be used as an adsorbent to adsorb, storage or separate a specific gas. Although there are no particular limitations thereon, the size of the pores of the porous metal complex (A) is preferably 2 Å to 50 Å, more preferably 2 Å to 30 Å, and even more preferably 2 Å to 20 Å, for example.

2-1. Metal Ions

Although there are no particular limitations on the metal ions that compose the metal complex (A) of the present invention provided they are able to form pores capable of containing specific molecules by organizing with the organic ligands, preferable examples thereof include cations of at least one type of metal selected from the group consisting of magnesium, calcium, aluminum, vanadium, manganese, iron, cobalt, nickel, copper, zinc, cadmium, lead and palladium. The metal ions are more preferably an ion of at least one type of metal selected from the group consisting of magnesium, aluminum, copper and zinc. The most preferable metal ions are a copper ion or zinc ion.

2-2. Organic Ligands

Although there are no particular limitations on the organic ligands that compose the metal complex (A) of the present invention provided they are an organic compound having two or more sites in a molecule thereof capable of coordination-bonding with the metal ions, and having an ability to construct a porous structure having a plurality of pores capable of containing specific molecules by organizing with the metal ions, they are preferably at least one organic compound selected from the group consisting of the following (1) to (3):

organic ligand (1): an organic compound having two or more carboxyl groups and/or hydroxyl groups, not having a heterocyclic ring, and capable of bidentate coordination with metal ions;

organic ligand (2): a saturated or unsaturated, monocyclic or polycyclic heterocyclic compound having a carboxyl group or hydroxyl group, having one heteroatom selected from N, O or S in a ring thereof, and capable of bidentate coordination with metal ions; and organic ligand (3): a saturated or unsaturated, monocyclic or polycyclic heterocyclic compound having two or more heteroatoms selected from N, O and S in one or a plurality of rings thereof, and capable of bidentate coordination with metal ions.

<Organic Ligand (1): Organic compound having two or more carboxyl groups and/or hydroxyl groups, not having a heterocyclic ring, and capable of bidentate coordination with metal ions>

Examples of the organic ligand (1) include alkylene dicarboxylic acid compounds having 4 to 20 carbon atoms (carbon atoms composing carboxyl groups are included in the number of carbon atoms), alkenylene dicarboxylic acid compounds having 4 to 20 carbon atoms (carbon atoms composing carboxyl groups are included in the number of carbon atoms), dicarboxylic acid compounds represented by the following general formulas (I) to (IV), and hydroxycarboxylic acid compounds represented by the following general formula (V).

The number of carbon atoms of an alkylene dicarboxylic acid compound having 4 to 20 carbon atoms (carbon atoms composing carboxyl groups are included in the number of carbon atoms) is preferably 4 to 10 and more preferably 4 to 6 from the viewpoint of pore size of the resulting complex. Specific examples thereof include succinic acid, glutaric acid and adipic acid. Among these, succinic acid is preferable.

The number of carbon atoms of an alkenylene dicarboxylic acid having 4 to 20 carbon atoms (carbon atoms composing carboxyl groups are included in the number of carbon atoms) is preferably 4 to 10 and more preferably 4 to 6 from the viewpoint of the pore size of the resulting complex. Specific examples thereof include fumaric acid, glutaconic acid and muconic acid (hexene dicarboxylic acid).

Dicarboxylic acid compounds represented by general formulas (I) to (III) are indicated with the following chemical formulas.

In formulas (I) to (III), $R^1$ respectively and independently represents a hydrogen atom, halogen atom, alkyl group having 1 to 4 carbon atoms, alkoxy group having 1 to 4 carbon atoms, formyl group, acyloxy group having 1 to 4 carbon atoms, alkoxycarbonyl group having an alkoxy group having 1 to 4 carbon atoms, nitro group, cyano group, carboxyl group, amino group, monoalkylamino group having 1 to 4 carbon atoms, dialkylamino group having an alkyl group having 1 to 4 carbon atoms or acylamino group having 1 to 4 carbon atoms, and two or more of $R^1$ may condense to form a ring. The two alkyl groups in the aforementioned dialkylamino group may be the same or different.

The halogen atom is preferably a fluorine atom or chlorine atom.

The alkyl group having 1 to 4 carbon atoms may be linear, branched or cyclic and examples thereof include a methyl group, ethyl group, propyl group, isopropyl group and butyl group, examples of the alkoxy group having 1 to 4 carbon atoms include a methoxy group, ethoxy group, propoxy group and butoxy group, examples of the acyloxy group having 1 to 4 carbon atoms include those substituted with a linear or branched alkyl group having 1 to 4 carbon atoms (such as an acetoxy group, propionyloxy group or isopropionyloxy group), examples of the alkoxycarbonyl group having an alkoxy group having 1 to 4 carbon atoms include those substituted with a linear or branched alkyl group having 1 to 4 carbon atoms (such as a methoxycarbonyl group, ethoxycarbonyl group, propoxycarbonyl group, isopropoxycarbonyl group or butoxycarbonyl group), examples of the monoalkylamino group having 1 to 4 carbon atoms include those substituted with a linear or branched alkyl group having 1 to 4 carbon atoms (such as a methylamino group, ethylamino group, propylamino group, isopropylamino group, butylamino group or isobutylamino group), examples of the dialkylamino group having an alkyl group having 1 to 4 carbon atoms include those substituted with a linear or branched alkyl group having 1 to 4 carbon atoms (such as a dimethylamino group, diethylamino group, dipropylamino group, diisopropylamino group or di-sec-butylamino group), and examples of the acylamino group having 1 to 4 carbon atoms include those substituted with a linear or branched alkyl group having 1 to 4 carbon atoms (such as an acetylamino group or propionylamino group). Among these, $R^1$ is preferably a hydrogen atom.

Dicarboxylic acid compounds represented by general formula (IV) are indicated with the following chemical formula.

(IV)

In formula (IV), $R^2$ respectively and independently represents a hydrogen atom, halogen atom or alkyl group having 1 to 4 carbon atoms, X represents a hydrogen atom, alkyl group having 1 to 4 carbon atoms, alkenyl group having 2 to 4 carbon atoms, alkynyl group having 2 to 4 carbon atoms, alkoxy group having 1 to 4 carbon atoms, nitro group, carboxyl group, hydroxyl group or amino group. The alkenyl group having 2 to 4 carbon atoms may be linear, branched or cyclic and examples thereof include a vinyl group, allyl group and crotyl group, and the alkynyl group having 2 to 4 carbon atoms may be linear or branched and examples thereof include an ethynyl group, propargyl group and butynyl group. Other specific examples of $R^2$ and X are the same as those explained with respect to the aforementioned $R^1$. Among these, $R^2$ is preferably a hydrogen atom. X is preferably a nitro group, hydrogen atom or methyl group from the viewpoint of raw material cost.

Hydroxycarboxylic acid compounds represented by general formula (V) are indicated with the following chemical formula.

(V)

In formula (V), $R^3$ respectively and independently represents a hydrogen atom, alkyl group having 1 to 4 carbon atoms, alkenyl group having 2 to 4 carbon atoms, alkynyl group having 2 to 4 carbon atoms or alkoxy group having 1 to 4 carbon atoms. Specific examples of $R^3$ are the same as those explained with respect to the aforementioned $R^1$ and $R^2$. Among these, $R^3$ is preferably a hydrogen atom.

The organic ligand (1) is preferably fumaric acid, terephthalic acid, isophthalic acid, 5-nitroisophthalic acid or methylisophthalic acid.

<Organic Ligand (2): Saturated or unsaturated, monocyclic or polycyclic heterocyclic compound having a carboxyl group or hydroxyl group, having one heteroatom selected from N, O or S in a ring thereof, and capable of bidentate coordination with metal ions>

Examples of the organic ligand (2) include organic compounds represented by the following general formulas (VI) to (VIII).

(VI)

(VII)

(VIII)

In formulas (VI) to (VIII), $R^3$ respectively and independently represents a hydrogen atom, alkyl group having 1 to 4 carbon atoms, alkenyl group having 2 to 4 carbon atoms, alkynyl group having 2 to 4 carbon atoms or alkoxy group having 1 to 4 carbon atoms. Specific examples of $R^3$ are the same as those explained with respect to the aforementioned $R^1$ and $R^2$. Among these, $R^3$ is preferably a hydrogen atom.

The organic ligand (2) is preferably pyridinedicarboxylic acid, isonicotinic acid or nicotinic acid.

<Organic Ligand (3): Saturated or unsaturated, monocyclic or polycyclic heterocyclic compound having two or more heteroatoms selected from N, O and S in one or a plurality of rings thereof, and capable of bidentate coordination with metal ions>

Examples of the organic ligand (3) include organic compounds represented by the following general formulas (IX) to (XII).

(IX)

(X)

(XI)

(XII)

In formulas (IX), (X) and (XII), Y represents an oxygen atom, sulfur atom, —$CH_2$—, —CH(OH)—, —CO—, —NH—, —$C_2N_4$— (1,2,4,5-tetrazine-3,6-diyl group), —C≡C—, —$C_2H_2$— or —$C_6H_4$—, and preferably represents —$C_2H_2$— or —$C_6H_4$—. $R^4$ respectively and independently represents a hydrogen atom, halogen atom, alkyl group having 1 to 4 carbon atoms, alkoxy group having 1 to 4 carbon atoms, formyl group, acyloxy group having 1 to 4 carbon atoms, alkoxycarbonyl group having an alkoxy group having 1 to 4 carbon atoms, nitro group, cyano group, carboxyl group, amino group, monoalkylamino group having 1 to 4 carbon atoms, dialkylamino group having an alkyl group having 1 to 4 carbon atoms or acylamino group having 1 to 4 carbon atoms. Specific examples of $R^4$ are the same as those explained with respect to the aforementioned $R^1$. n is an integer of 0 to 3 and preferably 0 or 1.

One type of the aforementioned organic ligands may be used alone or two or more types may be used in combination, and the organic ligands may be suitably selected corresponding to the type of gas targeted for adsorption. Among the aforementioned organic compounds, alkylene dicarboxylic acid compounds having 4 to 20 carbon atoms and organic compounds represented by general formula (I), general formula (IV), general formula (IX) and general formula (X) are preferable. More preferable examples include fumaric acid, terephthalic acid and derivatives thereof, isophthalic acid and derivatives thereof, pyrazine and derivatives thereof, 4,4'-bipyridine, 1,2-bis(4-pyridyl) ethane, 1,2-bis(4-pyridyl)ethylene and 1,2-bis(4-pyridyl) acetylene, while even more preferable examples include 1,3,5-benzenetricarboxylic acid, 5-nitroisophthalic acid, pyrazine, 2,3-pyrazinecarboxylic acid and 1,2-bis(4-pyridyl) ethylene.

In addition, in the case of using two or more types of organic ligands, there are no particular limitations on the combinations thereof. For example, combinations of organic ligands selected from the aforementioned organic ligand (1) and organic ligand (3), respectively, and combinations of two or more types of organic ligands selected from the aforementioned organic ligand (3) are preferable, while examples of more preferable combinations include combinations of organic compounds represented by general formula (I) and general formula (IX), combinations of organic compounds represented by general formula (IV) and general formula (IX), combinations of organic compounds represented by general formula (X) and general formula (IX), and combinations of two or more types of organic compounds represented by general formula (X), and even more preferable examples of combinations include a combination of 5-nitroisophthalic acid and 1,2-bis(4-pyridyl)ethylene and a combination of 2,3-pyrazinecarboxylic acid and pyrazine.

2-3. Production Method of Metal Complex (A)

The metal complex (A) is obtained by dissolving a metal salt of the aforementioned metal (such as a nitrate, sulfate, formate, acetate, carbonate, hydrochloride, hydrobromide, tetrafluoroborate or hexafluorophosphate) and the aforementioned organic ligand in water or an organic solvent and reacting for several hours to several days. The organic solvent is only required to dissolve the aforementioned metal salt and organic ligand in it, and examples of the solvents that can be used include methanol, ethanol, propanol, diethyl ether, tetrahydrofuran, hexane, cyclohexane, benzene, toluene, methylene chloride, chloroform, acetone, ethyl acetate, acetonitrile, dimethylsulfoxide (DMSO), N,N-dimethylformamide (DMF), water and mixed solvents of two or more types thereof. There are also no particular limitations on the reaction conditions, and although reaction conditions may be suitably adjusted depending on the degree to which the reaction proceeds, the reaction temperature is preferably, for example, room temperature (25° C.) to 150° C. In addition, the aforementioned reaction may also be carried out under pressure.

Although the metal complex (A) according to the present invention may be in various forms, such as granules, a powder, fibers, film or sheet, it is preferably in the form of a powder. The metal complex (A) having an average particle diameter of 1 μm to 500 μm (and more preferably at 5 μm to 100 μm) can be preferably used. In the present invention, "average particle diameter" refers to a diameter having a cumulative frequency of 50% (median diameter), and can be measured with, for example, a laser diffraction/scattering particle size distribution analyzer.

The amount of the metal complex (A) contained in the molded article for hydrocarbon adsorption of the present invention is preferably 50% by weight to 97% by weight. In consideration of adsorption performance and the productivity of the molded article for hydrocarbon adsorption, the content of the metal complex (A) is more preferably 70% by weight to 97% by weight. If the content of the metal complex (A) is less than 50% by weight, the adsorption efficiency of hydrocarbon gas per unit weight of a molded article is poor. On the other hand, if the content of the metal complex (A) exceeds 97% by weight, productivity of the molded article for hydrocarbon adsorption tends to decrease and the required strength will not be obtained.

3. Polymer Binder Component (B)

The polymer binder component (B) in the present invention is a component that functions as a binder that binds particles of the metal complex (A). From the viewpoint of binding the metal complex (A) so as to form a molded article for hydrocarbon adsorption, the polymer binder component (B) preferably has superior compatibility with hydrocarbons to be adsorbed. The polymer binder component (B) contains at least one functional group selected from the group consisting of a carboxyl group, hydroxyl group, amino group, mercapto group, epoxy group and sulfo group in a molecule thereof at 0.3 mmol/g to 8.0 mmol/g. The weight average molecular weight of the polymer binder component (B) is 1000 or more and preferably 5000 or more. The polymer binder component (B) preferably has a glass transition temperature (Tg) that is equal to or higher than the working temperature when carrying out an adsorption-desorption procedure for hydrocarbon adsorption using the molded article of the present invention.

The polymer binder component (B) contains at least one functional group selected from the group consisting of a carboxyl group, hydroxyl group, amino group, mercapto group, epoxy group and sulfo group in a molecule thereof at 0.3 mmol/g to 8.0 mmol/g. Among these functional groups, a hydroxyl group and carboxyl group are preferable in terms of interaction with metal. In the case a plurality of types of functional groups are present, the total amount thereof is within the aforementioned range. If the functional group content is less than 0.3 mmol/g, the strength of the molded article may be inadequate. On the other hand, if the functional group content exceeds 8.0 mmol/g, gas adsorption performance may decrease. The number (mmol) of functional groups per 1 g of polymer binder component can be measured by IR spectroscopy, NMR or other form of spectroscopy or by calculating from the composition used when producing the polymer binder component.

The polymer binder component (B) is preferably at least one type of an ethylenic hydrocarbon polymer, polyester, polyamide and polyether, and a copolymer of (meth)acrylic acid and a (meth)acrylic acid ester having 1 to 10 carbon atoms is particularly preferable. The term "(meth)acrylic acid" refers to either "acrylic acid" or "methacrylic acid".

Specific examples of ethylenic hydrocarbon polymers include partially saponified polyvinyl acetate, partially saponified polyvinyl butyrate, polyvinyl butyral resins, copolymers of methyl methacrylate and hydroxyethyl methacrylate, copolymers of methyl methacrylate and methacrylic acid, copolymers of ethyl methacrylate and methacrylic acid, copolymers of propyl methacrylate and methacrylic acid, copolymers of butyl methacrylate and methacrylic acid, copolymers of amyl methacrylate and methacrylic acid, copolymers of 2-ethylhexyl methacrylate and methacrylic acid, copolymers of methyl acrylate and hydroxyethyl acrylate, copolymers of methyl acrylate and acrylic acid, copolymers of ethyl acrylate and acrylic acid, copolymers of propyl acrylate and acrylic acid, copolymers of butyl acrylate and acrylic acid, partially saponified copolymers of ethylene and vinyl acetate, copolymers of ethylene and acrylic acid, copolymers of ethylene and methacrylic acid, copolymers of styrene and acrylic acid, copolymers of styrene and methacrylic acid, copolymers of methyl methacrylate and glycidyl methacrylate, copolymers of methyl acrylate and glycidyl acrylate, copolymers of ethylene and glycidyl methacrylate, copolymers of methyl methacrylate and dimethylaminoethyl methacrylate, copolymers of methyl acrylate and dimethylaminoethyl acrylate, copolymers of ethylene and dimethylaminoethyl methacrylate, copolymers of methyl methacrylate and styrene sulfonate and polymers of methyl methacrylate and vinyl sulfonate.

Examples of polyesters include polyethylene terephthalate, polybutylene terephthalate and polylactic acid. Examples of polyamides include Nylon 6® and Nylon-6,6®. Examples of polyethers include polyethylene glycol, polypropylene glycol, polyoxymethylene and polyphenylene ether. These polymers have a functional group on the terminal thereof. In the case the amount of the functional group does not satisfy the amount required in the present invention, functional groups can be introduced into the polymer by copolymerizing (co-condensing) a monomer having a functional group in a side chain thereof.

The aforementioned polymer binder component (B) may be used alone or two or more types may be used after mixing. In the case of a mixture, the total number of functional groups in the entire mixture is within the aforementioned range.

The amount of the polymer binder component (B) contained in the molded article for hydrocarbon adsorption of the present invention is preferably 3% by weight to 20% by weight. If the content of the polymer binder component (B) is less than 3% by weight, the strength of the molded article tends to be inadequate. On the other hand, if the content of the polymer binder component (B) exceeds 20% by weight, since the amount of the metal complex (A) contained in the molded article for hydrocarbon adsorption is relatively low, it may be difficult to obtain adequate adsorption performance. The content of the polymer binder component (B) is more preferably 5% by weight to 15% by weight and even more preferably 5% by weight to 12% by weight.

4. Lubricant (C)

A lubricant (C) may be used in the present invention to prevent defective tableting. There are no particular limitations on the lubricant (C) provided it is able to prevent tableting defects, such as capping during tableting. Specific examples of the lubricant (C) include graphite, boron nitride, stearic acid and stearic acid esters.

The amount of the lubricant (C) is preferably 0.1% by weight to 5% by weight, and more preferably 1% by weight to 4% by weight, based on a total of 100% by weight of the constituent components of the molded article for hydrocarbon adsorption. If the amount of the lubricant (C) is less than 0.1% by weight, capping and other tableting defects could not be prevented and the yield of the molded article may be poor. On the other hand, if the amount of the lubricant (C) exceeds 5% by weight, the strength of the molded article may be inadequate, or since the amount of the metal complex (A) in the molded article for hydrocarbon adsorption is relatively low, it may be difficult to obtain adequate adsorption performance.

5. Other Components

The molded article for hydrocarbon adsorption of the present invention may also contain other additives in addition to the metal complex (A), the polymer binder component (B) and the lubricant (C). Examples of additives include glass fibers used for the purpose of improving the mechanical strength of the molded article, polymer coagulants and pigments. The amounts of these components used is preferably 0% by weight to 10% by weight (and more preferably 0% by weight to 3% by weight) based on a total of 100% by weight of the constituent components of an adsorption sheet.

6. Method for Producing Molded Article for Hydrocarbon Adsorption

Although there are no particular limitations on the method used to produce the molded article for hydrocarbon adsorption of the present invention, an example thereof is a tableting method. In the case of fabricating pellets with a tableting method, the metal complex (A), polymer binder component (B) and other components are first mixed at a prescribed blending ratio and then granulated. At this time, the components may be mixed while adding a solvent by spraying and the like so as to dissolve the polymer binder component therein, or a solution of the polymer binder component may be added followed by mixing while evaporating the solvent.

Next, the resulting granulated substances are mixed with the optionally used lubricant (C) and other components at a prescribed blending ratio followed by tableting with a tableting machine at a predetermined pressure.

The pellets resulting from tableting are preferably subjected to annealing treatment in order to remove water and the like contained during the production process and the like. Although the temperature during annealing treatment is a temperature equal to or higher than the temperature at which water and the like can be removed, crushing strength of the molded article may be advantageously improved if the temperature is equal to or higher than the glass transition temperature of the polymer binder component (B).

The size of the molded article for hydrocarbon adsorption of the present invention is preferably 0.5 mm to 5 mm, more preferably 1 mm to 3 mm and even more preferably 1.6 mm to 2 mm. If the size of the molded article is excessively small, the strength of the molded article may be inadequate and the productivity may be decreased. If the size is excessively large, the adsorbed amount per unit time may decrease due to the slow diffusion within the molded article.

7. Adsorption-Desorption Procedure

Since the molded article for hydrocarbon adsorption of the present invention has the metal complex (A), which can selectively adsorb only a specific hydrocarbon gas accompanying a change in the structure and/or size thereof and adsorb and desorb the hydrocarbon gas by the change of pressure, it demonstrates superior performance for separating a specific hydrocarbon gas from a mixed gas. In addition, since the components that compose the molded article for hydrocarbon adsorption are comparatively flexible and can accommodate structural changes of the metal complex (A), the molded article can demonstrate the superior performance of the metal complex (A) even when in the form of a molded article for hydrocarbon adsorption. Consequently, the molded article for hydrocarbon adsorption of the present invention is preferably used as an adsorbent in, for example, a pressure swing adsorption type of gas separation apparatus.

EXAMPLES

Although the following provides a more detailed explanation of the present invention through examples thereof, the present invention is not limited by these examples, and can obviously be carried out while suitably adding modifications within a range in accordance with the gist of the present disclosure, and all such modifications are included within the scope of the present invention.

1. Production of Molded Article 200 parts by weight of tetrahydrofuran were mixed with prescribed amounts of the metal complex (A) and the polymer binder component (B) based on 100 parts by weight of the total amount of the metal complex (A), the polymer binder component (B) and the lubricant (C) followed by kneading with a mortar and crushing while air-drying to obtain granulated substances that passed through a 0.75 mm mesh sieve. Graphite as the lubricant (C) was added so that the amount thereof in the molded article was 3 parts by weight based on 100 parts by weight of the molded article followed by mixing well and tableting the resulting mixture at a tableting pressure of 600 MPa using a tableting machine to produce cylindrical molded articles (pellets) having a thickness of about 4 mm and a diameter of 3 mm. The resulting molded articles were used in each of the following tests after vacuum drying at 150° C. and 50 Pa for 6 hours or more to remove adsorbed water and like.

2. Evaluation Methods 2-1. Adsorption-Desorption Isotherms

Adsorption-desorption isotherms were prepared by measuring the metal complexes or molded articles (pellets) used in the examples and comparative examples using a gas adsorption measuring apparatus (BELSORP®-HP manufactured by Bell Japan Inc. or BELSORP®-18HT manufactured by Bell Japan Inc.) according to the volumetric method (equilibration pause time: 500 seconds) at 25° C. Each sample was measured such that the amount of porous metal complex in the samples was 0.3 to 0.5 g.

2-2. Effective Adsorption Amount

The metal complexes and molded articles (pellets) obtained in the examples and comparative examples were dried under reduced pressure for 6 hours or more at 150° C. and 50 Pa to remove adsorbed water and the like. After temporarily adsorbing gas using a gas adsorption apparatus (BELSORP®-HP manufactured by Bell Japan Inc.) and holding for a prescribed period of time (reduced pressure holding time) under reduced pressure at 25° C. and 50 Pa, adsorbed amounts were measured at 25° C. and 140 Pa according to the volumetric method (equilibration pause time: 300 seconds) and converted to the adsorbed amount per unit weight, which was used as the "effective adsorption amount". The ratio of the effective adsorption amount per unit weight of the metal complex in the molded article to the effective adsorption amount of the original metal complex was calculated as the retention rate (%). Since the rates of adsorption and desorption vary according to the type of metal complex, the reduced pressure holding time changes for each type of metal complex. The reduced pressure holding time was 1 minutes for the fast adsorbing and desorbing metal complex, and 10 minutes for the slow adsorbing and desorbing metal complex.

2-3. Crushing Strength

After the gas adsorption measurements, a load was applied to the side of the cylindrical molded articles using the Model THK-20N Kiya Digital Hardness Tester manufactured by Fujiwara Scientific Co., Ltd., followed by measurement of the value when the molded article broke. Five molded articles were measured and the resulting average value thereof was used as the value of crushing strength.

3. Metal Complex (A)

3-1. Synthesis of Metal Complex (1): $[Cu_2(pzdc)_2(prz)]$

Copper sulfate trihydrate (1.23 g, 5.0 mmol, 1.0 eq.), pyrazine (4.05 g, 50.0 mmol, 10.0 eq.) and pure water (100 ml) were added to a recovery flask (500 ml) and mixed. To this resulting clear blue solution, a mixture of an aqueous solution (80 ml) of 2,3-pyrazine dicarboxylic acid (0.84 g, 5.0 mmol, 1.0 eq.) and a 1 N aqueous NaOH solution (20 ml) was added dropwise. After stirring the mixed solution for 2 hours at room temperature (25° C.), the resulting blue solid was filtered with a Kiriyama® funnel, washed with pure water and methanol in that order and then dried to obtain a blue powder (Metal Complex (1)) (yield: 1.32 g). A laser diffraction/scattering particle size distribution analyzer (Partica® LA-950VS manufactured by Horiba, Ltd.) revealed that the average particle diameter of Metal Complex (1) was 23 μm. In the aforementioned formula, "prz" refers to pyrazine, while "pzdc" refers to 2,3-pyrazine dicarboxylic acid.

Figure 8:
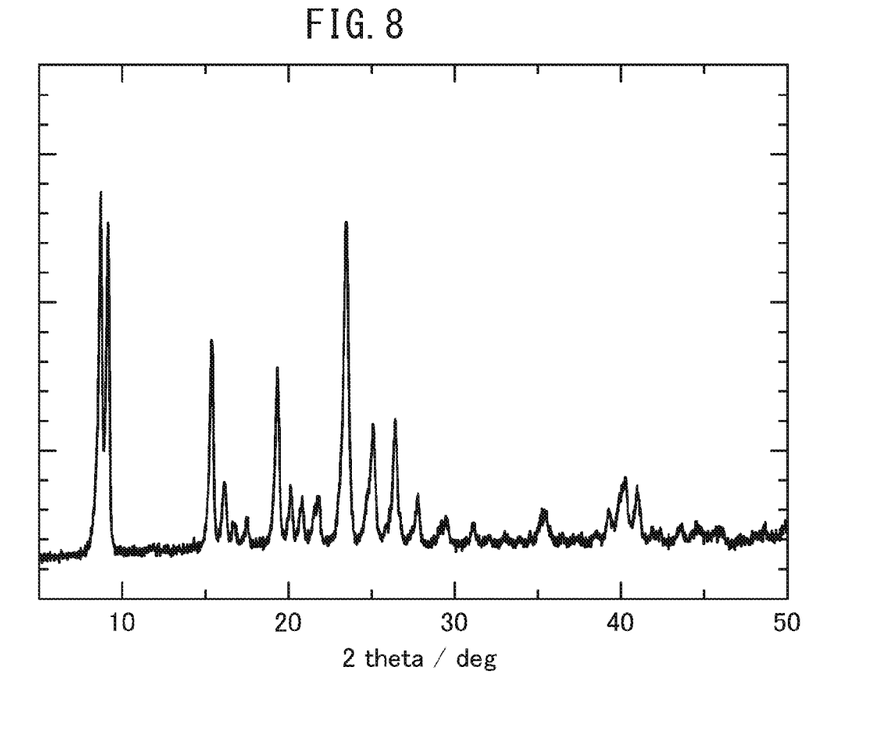
FIG. 8 is a powder X-ray diffraction pattern of a metal complex (1).

The powder X-ray diffraction pattern of the resulting Metal Complex (1) was measured. The powder X-ray diffraction pattern was measured according to a symmetrical reflection method at a scanning rate of 3°/minute over a diffraction angle range (2θ) of 3° to 50° using an X-ray diffraction system (MultiFlex manufactured by Rigaku Corp.). The measurement results are shown in FIG. 8.

3-2. Synthesis of Metal Complex (2): [Zn(NO$_2$-ip) (bpe)]

Zinc nitrate hexahydrate (1.50 g, 5.04 mmol, 1.0 eq.), 5-nitroisophthalic acid (1.07 g, 5.07 mmol, 1.0 eq.), 1,2-bis (4-pyridyl)ethylene (0.91 g, 5.01 mmol, 1.0 eq.) and DMF (100 ml) were added to a recovery flask (300 ml) followed by heating for 16 hours at 120° C. (in an N$_2$ gas atmosphere). The resulting white solid was filtered with a Kiriyama® funnel, washed with DMF and methanol in that order and then dried to obtain a white powder (Metal Complex (2)) (yield: 2.3 g, average particle diameter: 63 μm). In the aforementioned formula, "NO$_2$-ip" refers to 5-nitroisophthalic acid, while "bpe" refers to 1,2-bis(4-pyridyl) ethylene.

Figure 9:
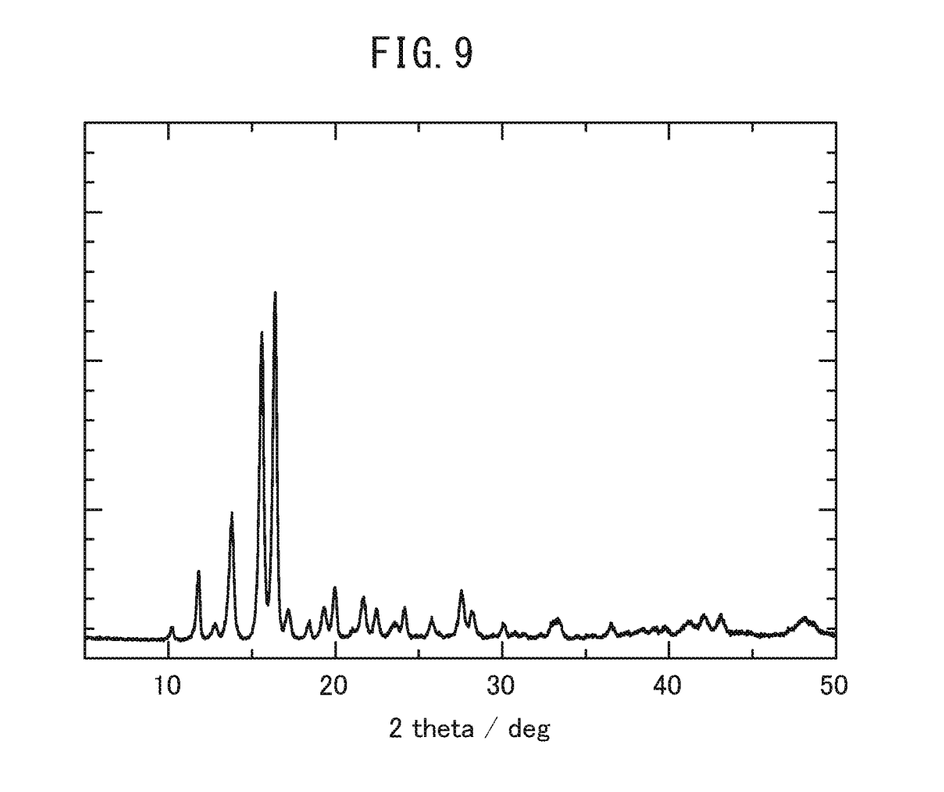
FIG. 9 is a powder X-ray diffraction pattern of a metal complex (2).

The powder X-ray diffraction pattern of the resulting Metal Complex (2) was measured in the manner described above. The results are shown in FIG. 9.

4. Polymer Binder Component (B)

The used polymer binder components (B) were as indicated below.

Polymer Binder 1: MMA/MAA-1

Copolymer of methyl methacrylate and methacrylic acid (95:5 (molar ratio), Polysciences Inc.)

Tg=116.8° C.

Functional group: Carboxyl group, 0.50 mmol/g

Polymer Binder 2: MMA/MAA-2

Copolymer of methyl methacrylate and methacrylic acid (75:25 (molar ratio), Polysciences Inc.)

Tg=150° C.

Functional group: Carboxyl group, 2.59 mmol/g

Polymer Binder 3: PMAA

Poly(methacrylic acid) (Polysciences Inc.)

Tg=228° C.

Functional group: Carboxyl group, 11.62 mmol/g

Polymer Binder 4: PMMA

Poly(methyl methacrylate) (Wako Pure Chemical Industries, Ltd.)

Tg=103.3° C.

Functional group: None, 0 mmol/g

Polymer Binder 5: PVAc/OH

88% saponified polyvinyl acetate

Tg=67.8° C.

Functional group: Hydroxyl group, 17.9 mmol/g

Polymer Binder 6: PVAc

Polyvinyl acetate

Tg=41.9° C.

Functional group: None, 0 mmol/g

5. Lubricant (C)

Graphite (ACP, Nippon Graphite Industries, Ltd.) was used for the Lubricant (C).

Example 1

Molded Article (1)

By mixing 87 parts by weight of Metal Complex (1) and 10 parts by weight of Polymer Binder 1 (MMA/MAA-1) based on the composition of a molded article with 200 parts by weight of tetrahydrofuran followed by kneading with a mortar and crushing while air-drying, granulated substances that passed through a 0.5 mm mesh sieve were obtained. Graphite as the lubricant (C) was added so that the amount thereof in the molded article was 3 parts by weight based on 100 parts by weight of the molded article followed by mixing well and producing a molded article at room temperature using a tableting machine. The resulting molded article was dried under reduced pressure for 6 hours or more at 150° C. and 50 Pa to remove adsorbed water and like and was designated as Molded Article (1).

Evaluation of Adsorption Characteristics

Figure 1:
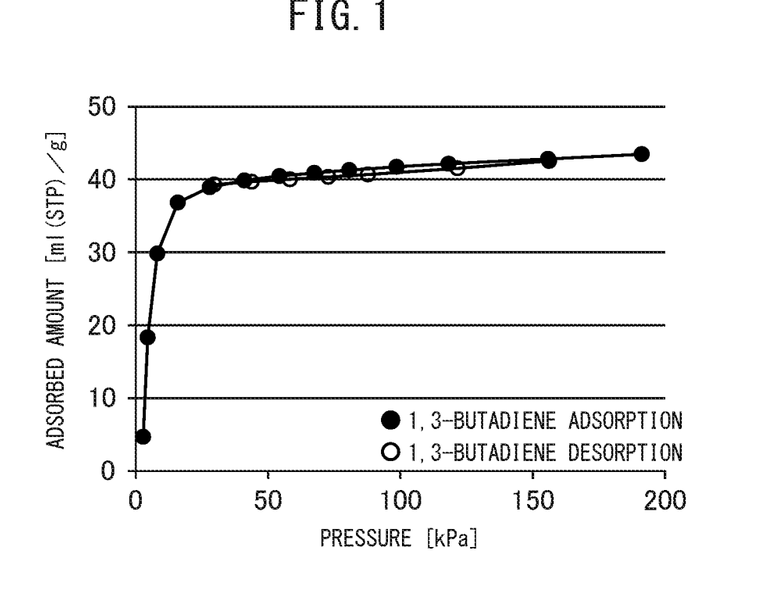
FIG. 1 is an adsorption-desorption isotherm of a metal complex (1) with respect to 1,3-butadiene at 25° C.
Figure 2:
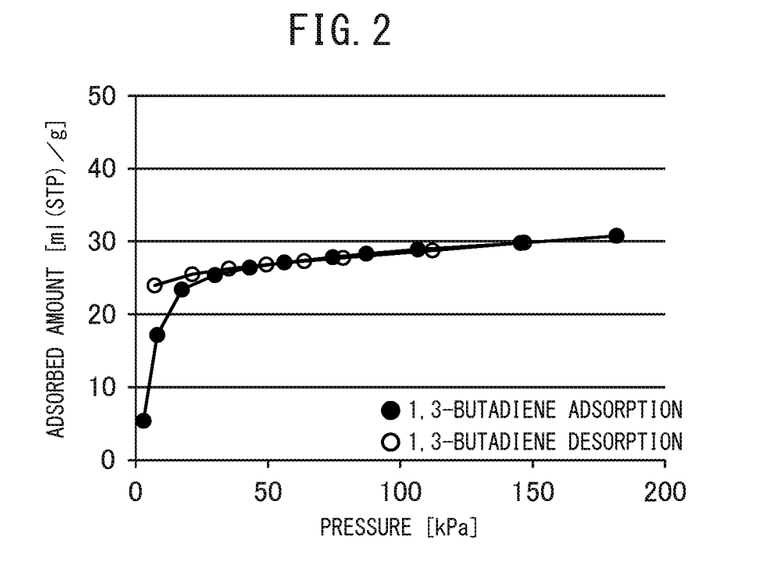
FIG. 2 is an adsorption-desorption isotherm of a molded article (1) of Example 1 with respect to 1,3-butadiene at 25° C.
Figure 3:
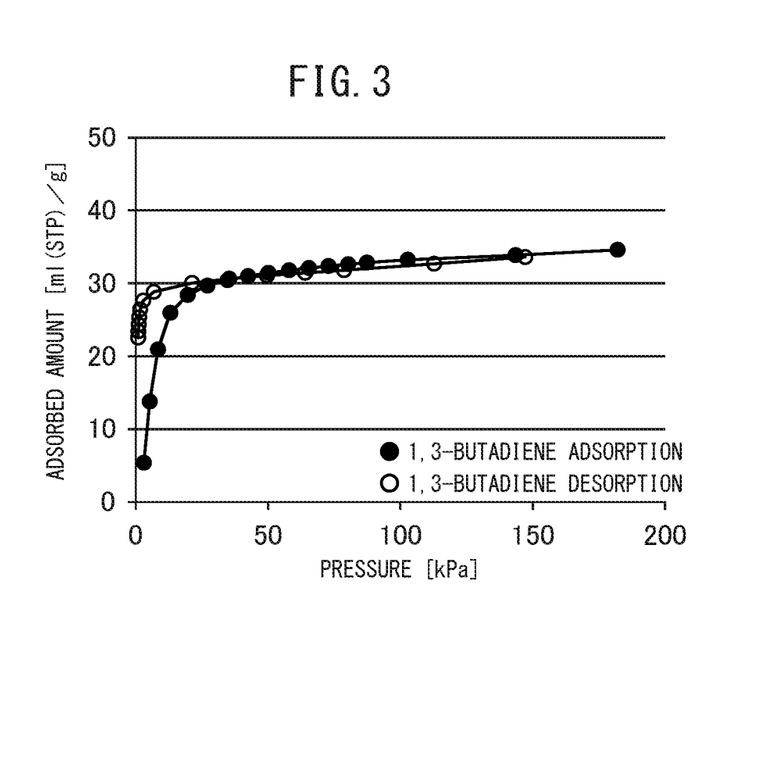
FIG. 3 is an adsorption-desorption isotherm of a molded article (2) of Example 2 with respect to 1,3-butadiene at 25° C.

The adsorption-desorption isotherm for 1,3-butadiene was measured at 25° C. for the Metal Complex (1) and Molded Article (1). The results are shown in FIGS. 1 and 2. The adsorbed amount of the target gas (1,3-butadiene) per unit weight is plotted on the vertical axis. This applies similarly to FIGS. 3 to 7. The effective adsorption amounts of the Metal Complex (1) and the Molded Article (1) with respect to 1,3-butadiene were 15.9 ml (STP)/g and 13.2 ml (STP)/g, respectively, when a reduced pressure holding time was 10 minutes.

Based on a comparison of FIG. 1 and FIG. 2, the adsorbed amounts of 1,3-butadiene of the Metal Complex (1) and Molded Article (1) at a pressure of 180 kPa were 43 ml (STP) and 30 ml (STP), respectively. The adsorption amount of the Molded Article (1) was 69% that of the Metal Complex (1). This value is equivalent to a value of 80% when compared on the basis of the adsorbed amount per unit weight of the Metal Complex (1) contained in the Molded Article (1). In addition, the effective adsorption amount of the Molded Article (1) was 83% that of the Metal Complex (1), and it can therefore be understood that an amount of 1,3-butadiene was adsorbed that is equivalent to 95% per unit weight of the metal complex (retention rate). From this result, it is clear that the molded article of the present invention does not significantly impair the adsorption performance of a powder of the porous metal complex and is superior as an adsorbent.

Evaluation of Strength

When crushing strength was measured for the Molded Article (1) following completion of measurement of adsorption of 1,3-butadiene, it was found to be 108 N. It is clear that the molded article of the present invention has practical strength and is superior as an adsorbent and separating material.

The above results are summarized in Table 1.

Examples 2 to 4 and Comparative Examples 1 to 7

Molded articles were produced in the same manner as Example 1 with the exception of using the conditions indicated in Table 1, after which they were used in each of the evaluation tests. The results are shown in Table 1. In addition, the 1,3-butadiene adsorption-desorption isotherms at 25° C. of the Molded Article (2) of Example 2, Metal Complex (2), Molded Article (3) of Example 3, Molded Article (4) of Example 4 and Molded Article (11) of Comparative Example 7 are respectively shown in FIGS. 3 to 7.

According to the results of Examples 1, 2, 3 and 4, each of the molded articles of the present invention did not significantly impair adsorption performance of the original metal complex in the powdered state and were determined to have practical strength. From these results, it is clear that each molded article of the present invention is superior as an adsorbent.

The effective adsorption amount of 1,3-butadiene of the Molded Article (5) of Comparative Example 1 was only 50% of the effective adsorption amount of the Metal Complex (1) used. This would be due to the polymer binder component in the Molded Article (5), which was produced using poly(methacrylic) acid for the polymer binder component, having difficulty in permeating 1,3-butadiene, thereby preventing the porous Metal Complex (1) from delivering its inherent adsorption performance. From this result, it is clear that a molded article produced using a polymer binder component having an excess of functional groups impairs the adsorption performance of the porous Metal Complex (1).

The crushing strength of the Molded Article (6) of Comparative Example 2 was low in comparison with those of Example 1 and Example 2. Thus, it is clear that the strength of a molded article produced using a polymer binder component not having an adequate number of functional groups is inferior.

The effective adsorption amount of 1,3-butadiene of the Molded Article (7) of Comparative Example 3 was only 27% of the effective adsorption amount of the Metal Complex (1) used. This would be due to the polymer binder component in the Molded Article (7), which was produced using 88% saponified polyvinyl acetate for the polymer binder component, being unable to permeate 1,3-butadiene, thereby preventing the Metal Complex (1) from delivering its inherent adsorption performance. From this result, it is clear that a molded article produced using a polymer binder component having an excess of functional groups impairs the adsorption performance of the porous Metal Complex (1).

The effective adsorption amount of 1,3-butadiene of the Molded Article (8) of Comparative Example 4 was only 13% of the effective adsorption amount of the Metal Complex (2) used. This would be due to the polymer binder component in the Molded Article (8), which was produced using poly(methacrylic acid) for the polymer binder component, having difficulty in permeating 1,3-butadiene, thereby preventing the Metal Complex (2) from delivering its inherent adsorption performance. From this result, it is clear that a molded article produced using a polymer binder component having an excess of functional groups impairs the adsorption performance of the porous Metal Complex (2).

The crushing strength of the Molded Article (9) of Comparative Example 5 was low in comparison with that of Example 3 having a similar polymer binder component composition. Thus, it has proved that a molded article produced using a polymer binder component not having an adequate number of functional groups has inferior strength. The crushing strength of the Molded Article (10) of Comparative Example 6, which used PVAc, which has comparatively low material strength when used alone, for the polymer binder component, was low in comparison with those of both Example 3 and Example 4. Thus, it has proved that a molded article produced using a polymer binder component not having an adequate number of functional groups has inferior strength.

Figure 4:
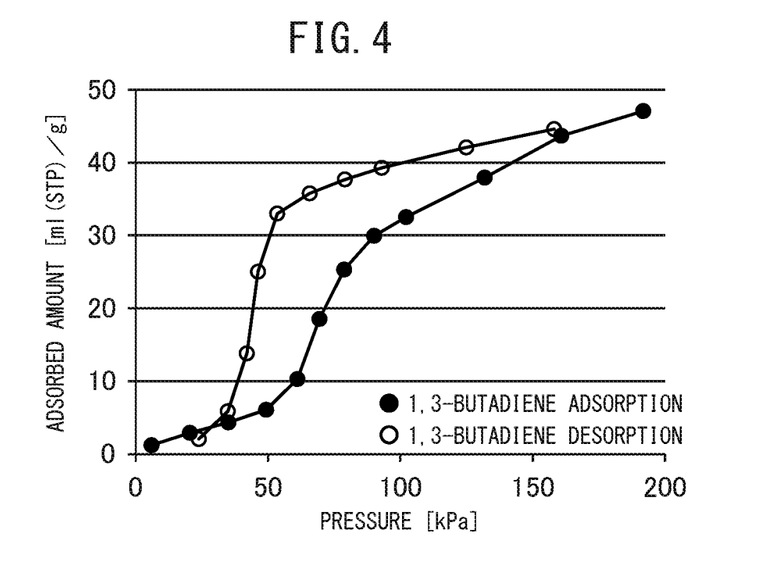
FIG. 4 is an adsorption-desorption isotherm of a metal complex (2) with respect to 1,3-butadiene at 25° C.
Figure 5:
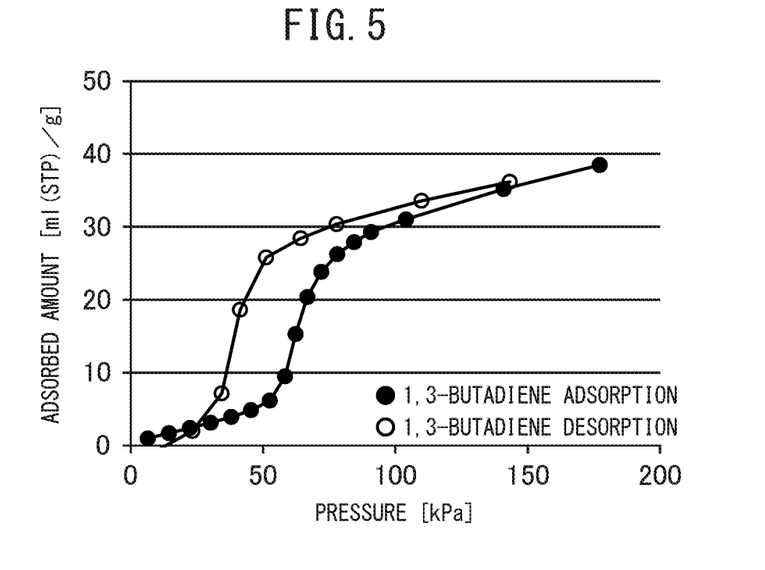
FIG. 5 is an adsorption-desorption isotherm of a molded article (3) of Example 3 with respect to 1,3-butadiene at 25° C.
Figure 6:
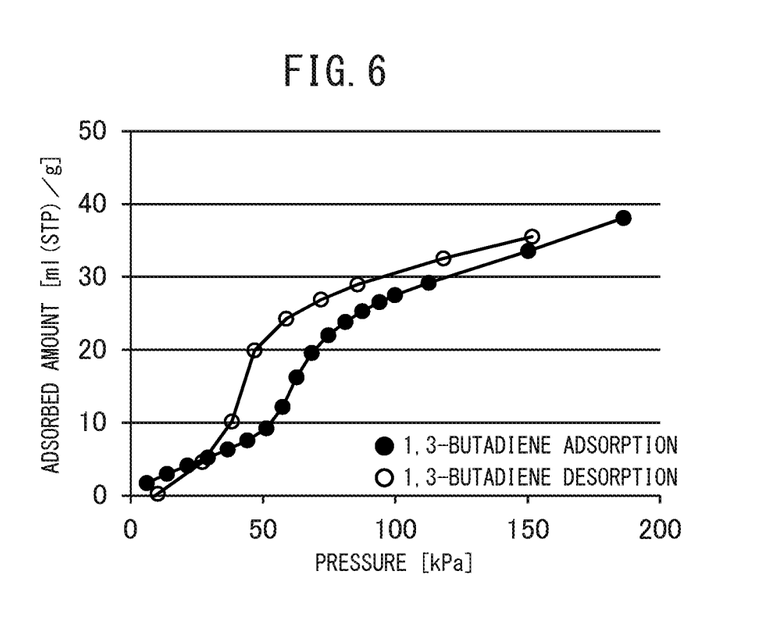
FIG. 6 is an adsorption-desorption isotherm of a molded article (4) of Example 4 with respect to 1,3-butadiene at 25° C.
Figure 7:
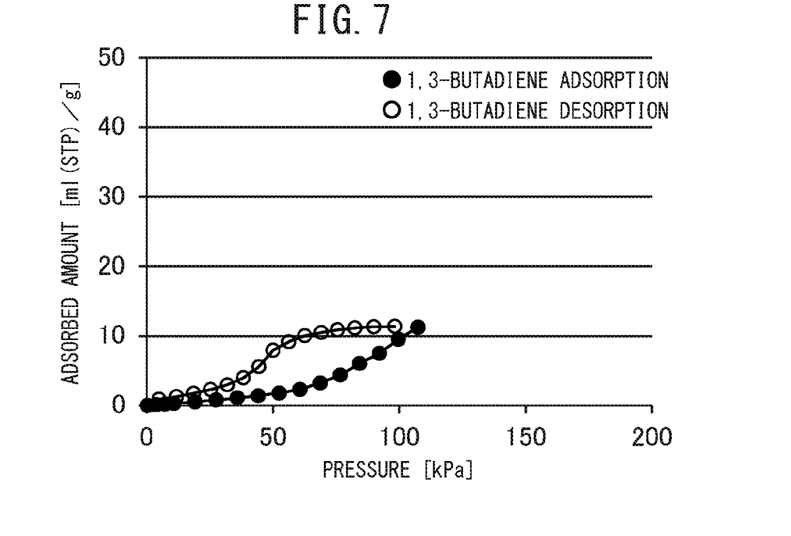
FIG. 7 is an adsorption-desorption isotherm of a molded article (11) of Comparative Example 7 with respect to 1,3-butadiene at 25° C.

The adsorbed amount of 1,3-butadiene of the Molded Article (11) of Comparative Example 7 was only about 30% of the adsorbed amount per unit weight of the Metal Complex (2) used based on a comparison of FIG. 4 and FIG. 7. This would be due to the polymer binder component in the Molded Article (11), which was produced using 88% saponified polyvinyl acetate for the polymer binder component, being unable to permeate 1,3-butadiene, thereby preventing the Metal Complex (2) from delivering its inherent adsorption performance. From this result, it is clear that a molded article produced using a polymer binder component having an excess of functional groups impairs the adsorption performance of the Metal Complex (2).

TABLE 1

|  |  | Ex. 1 | Ex. 2 | Ex. 3 | Ex. 4 | Comp. Ex. 1 | Comp. Ex. 2 |
|---|---|---|---|---|---|---|---|
| Metal Complex (A)[1] |  | Metal Complex (1) | | Metal Complex (2) | | Metal Complex (1) | |
|  | Core metal | Cu | | Zn | | Cu | |
|  | Organic ligand (1) |  | | NO$_2$-ip | |  | |
|  | Organic ligand (2) |  | |  | |  | |
|  | Organic ligand (3) | prz/pzdc | | bpe | | prz/pzdc | |
| Polymer Binder Component (B)[1] |  | MMA/MAA-1 | MMA/MAA-2 | MMA/MAA-1 | MMA/MAA-2 | PMAA | PMMA |
|  | Functional group | COOH | COOH | COOH | COOH | COOH | None |
|  | Functional group amount (mmol/g) | 0.50 | 2.59 | 0.50 | 2.59 | 11.62 | 0 |
|  | Tg(° C.) | 116.8 | 150.0 | 116.8 | 150.0 | 228.0 | 103.3 |
| Lubricant (C) |  | Graphite | | | | | |
| Molded Article No. |  | (1) | (2) | (3) | (4) | (5) | (6) |
| Composition (wt %) | Metal Complex (A) | 87.0 | 87.0 | 89.5 | 89.5 | 87.0 | 87.0 |
|  | Binder (B) | 10.0 | 10.0 | 7.5 | 7.5 | 10.0 | 10.0 |
|  | Lubricant (C) | 3.0 | 3.0 | 3.0 | 3.0 | 3.0 | 3.0 |
| Adsorption-desorption isotherm (1,3-BD) | Measuring pressure(kPa) | 180 | 180 | 180 | 180 |  |  |
|  | Metal complex (ml/g) | 43 | 43 | 46 | 46 |  |  |
|  | Molded article (ml/g) | 30 | 35 | 38 | 38 |  |  |
|  | Retention rate (%)[2] | 78 | 81 | 83 | 83 |  |  |
|  | Dwg. No. (metal complex) | 1 | 1 | 4 | 4 | 1 | 1 |
|  | Dwg. No. (molded article) | 2 | 3 | 5 | 6 | None | None |
| Effective adsorption amount (1,3-BD) | Metal complex (ml/g) | 13.2 | 13.2 | 26.1 | 26.1 | 13.2 | 13.2 |
|  | Molded article (ml/g) | 15.9 | 9.1 | 20.4 | 20.6 | 8.0 | 11.3 |
|  | Reduced pressure holding time (min) | 10 | 10 | 1 | 1 | 10 | 10 |
|  | Retention rate (%)[2] | 95 | 70 | 87 | 88 | 50 | 82 |
| Molded article | Crushing strength (N) | 108 | 71.7 | 52.1 | 38.4 | 76 | 57 |

|  |  | Comp. Ex. 3 | Comp. Ex. 4 | Comp. Ex. 5 | Comp. Ex. 6 | Comp. Ex. 7 |
|---|---|---|---|---|---|---|
| Metal Complex (A)[1] |  | Metal Complex (1) | | Metal Complex (2) | | |
|  | Core metal | Cu | | Zn | | |
|  | Organic ligand (1) |  | | NO$_2$-ip | | |
|  | Organic ligand (2) |  | | | | |
|  | Organic ligand (3) | prz/pzdc | | bpe | | |

TABLE 1-continued

| | | | | | | |
|---|---|---|---|---|---|---|
| Polymer Binder Component (B)[1]) | | PVAc/OH | PMAA | PMMA | PVAc | PVAc/OH |
| | Functional group | OH | COOH | None | None | OH |
| | Functional group amount (mmol/g) | 17.90 | 11.62 | 0 | 0 | 17.90 |
| | Tg(° C.) | 67.8 | 228.0 | 103.3 | 41.9 | 67.8 |
| Lubricant (C) | | | | Graphite | | |
| Molded Article No. | | (7) | (8) | (9) | (10) | (11) |
| Compo- | Metal Complex (A) | 87.0 | 89.5 | 89.5 | 90.0 | 90.0 |
| sition (wt %) | Binder (B) | 10.0 | 7.5 | 7.5 | 7.0 | 7.0 |
| | Lubricant (C) | 3.0 | 3.0 | 3.0 | 3.0 | 3.0 |
| Adsorption- | Measuring pressure(kPa) | | | | | 100 |
| desorption | Metal complex (ml/g) | | | | | 33 |
| isotherm | Molded article (ml/g) | | | | | 10 |
| (1,3-BD) | Retention rate (%)[2]) | | | | | 30 |
| | Dwg. No. (metal complex) | 1 | 4 | 4 | 4 | 4 |
| | Dwg. No. (molded article) | None | None | None | None | 7 |
| Effective | Metal complex (ml/g) | 13.2 | 26.1 | 26.1 | 26.1 | 26.1 |
| adsorption | Molded article (ml/g) | 4.3 | 3.3 | 19.5 | 17.6 | 3.5 |
| amount | Reduced pressure holding time (min) | 10 | 1 | 1 | 1 | 1 |
| (1,3-BD) | Retention rate (%)[2]) | 27 | 13 | 83 | 75 | 15 |
| Molded article | Crushing strength (N) | 144 | 54 | 44 | 26 | 47 |

[1])Metal Complex (1): $Cu_2(pzdc)_2(prz)$, Metal Complex (2): $Zn(NO_2\text{-ip})(bpe)$, prz: pyrazine, pzdc: 2,3-pyrazine dicarboxylic acid, $NO_2$-ip: 5-nitroisophthalic acid, bpe: 1,2-bis(4-pyridyl)ethylene, 1,3-BD: 1,3-butadiene, MMA/MAA-1: methyl methacrylate/methacrylic acid copolymer (95:5), MMA/MAA-2: methyl methacrylate/methacrylic acid copolymer (75:25), PMAA: poly(methacrylic acid), PMMA: poly(methyl methacrylate), PVAc: polyvinyl acetate, PVAc/OH: 88% saponified polyvinyl acetate
[2])Retention rate per unit weight of metal complex (%)

The invention claimed is:

1. A molded article for hydrocarbon adsorption comprising a metal complex (A), composed of metal ions and organic ligands capable of bonding with the metal ions; and a polymer binder component (B), which contains at least one functional group selected from the group consisting of a carboxyl group, hydroxyl group, amino group, mercapto group, epoxy group and sulfo group at a total of 0.3 mmol/g to 8.0 mmol/g in a molecule thereof.

2. The molded article for hydrocarbon adsorption according to claim 1, wherein a functional group of the polymer binder component (B) is a hydroxyl group or carboxyl group.

3. The molded article for hydrocarbon adsorption according to claim 1, wherein the polymer binder component (B) is an ethylenic hydrocarbon polymer, polyester, polyamide or polyether.

4. The molded article for hydrocarbon adsorption according to claim 1, wherein the polymer binder component (B) is a copolymer of a (meth)acrylic acid ester having 1 to 10 carbon atoms and (meth)acrylic acid.

5. The molded article for hydrocarbon adsorption according to claim 1, which contains 50% by weight to 97% by weight of the metal complex (A).

6. The molded article for hydrocarbon adsorption according to claim 1, wherein the organic ligands are at least one organic compound selected from the group consisting of the following (1) to (3):
   organic ligand (1): an organic compound having two or more carboxyl groups and/or hydroxyl groups, not having a heterocyclic ring, and capable of bidentate coordination with the metal ions;
   organic ligand (2): a saturated or unsaturated, monocyclic or polycyclic heterocyclic compound having a carboxyl group or hydroxyl group, having one heteroatom selected from N, O or S in a ring thereof, and capable of bidentate coordination with the metal ions; and
   organic ligand (3): a saturated or unsaturated, monocyclic or polycyclic heterocyclic compound having two or more heteroatoms selected from the group consisting of N, O and S in one or a plurality of rings thereof, and capable of bidentate coordination with the metal ions.

7. The molded article for hydrocarbon adsorption according to claim 6, wherein the organic ligand (1) is at least one type selected from the group consisting of an alkylene dicarboxylic acid compound having 4 to 20 carbon atoms, an alkenylene dicarboxylic acid compound having 4 to 20 carbon atoms, a dicarboxylic acid compound represented by the following general formulas (I) to (IV), and a hydroxycarboxylic acid compound represented by the following general formula (V):

wherein $R^1$ respectively and independently represents a hydrogen atom, halogen atom, alkyl group having 1 to 4 carbon atoms, alkoxy group having 1 to 4 carbon atoms, formyl group, acyloxy group having 1 to 4 carbon atoms, alkoxycarbonyl group having an alkoxy group having 1 to 4 carbon atoms, nitro group, cyano group, carboxyl group, amino group, monoalkylamino group having 1 to 4 carbon atoms, dialkylamino group having an alkyl group having 1 to 4 carbon atoms or acylamino group having 1 to 4 carbon atoms, and two or more of $R^1$ may condense to form a ring;

(IV)

wherein $R^2$ respectively and independently represents a hydrogen atom, halogen atom or alkyl group having 1 to 4 carbon atoms, X represents a hydrogen atom, alkyl group having 1 to 4 carbon atoms, alkenyl group having 2 to 4 carbon atoms, alkynyl group having 2 to 4 carbon atoms, alkoxy group having 1 to 4 carbon atoms, nitro group, carboxyl group, hydroxyl group or amino group; and

(V)

wherein $R^3$ respectively and independently represents a hydrogen atom, alkyl group having 1 to 4 carbon atoms, alkenyl group having 2 to 4 carbon atoms, alkynyl group having 2 to 4 carbon atoms or alkoxy group having 1 to 4 carbon atoms.

8. The molded article for hydrocarbon adsorption according to claim 6, wherein the organic ligand (2) is at least one type selected from the group consisting of compounds represented by the following general formulas (VI) to (VIII):

(VI)

(VII)

(VIII)

wherein $R^3$ respectively and independently represents a hydrogen atom, alkyl group having 1 to 4 carbon atoms, alkenyl group having 2 to 4 carbon atoms, alkynyl group having 2 to 4 carbon atoms or alkoxy group having 1 to 4 carbon atoms.

9. The molded article for hydrocarbon adsorption according to claim 6, wherein the organic ligand (3) is at least one type selected from the group consisting of compounds represented by the following general formulas (IX) to (XII):

(IX)

(X)

(XI)

(XII)

wherein Y represents an oxygen atom, sulfur atom, —$CH_2$—, —CH(OH)—, —CO—, —NH—, —$C_2N_4$—, —C≡C—, —$C_2H_2$— or —$C_6H_4$—, $R^4$ respectively and independently represents a hydrogen atom, halogen atom, alkyl group having 1 to 4 carbon atoms, alkoxy group having 1 to 4 carbon atoms, formyl group, acyloxy group having 1 to 4 carbon atoms, alkoxycarbonyl group having an alkoxy group having 1 to 4 carbon atoms, nitro group, cyano group, carboxyl group, amino group, monoalkylamino group having 1 to 4 carbon atoms, dialkylamino group having an alkyl group having 1 to 4 carbon atoms or acylamino group having 1 to 4 carbon atoms, and n is an integer of 0 to 3.

10. The molded article for hydrocarbon adsorption according to claim 1, wherein the metal ions are a copper ion or zinc ion.

11. The molded article for hydrocarbon adsorption according to claim 1, wherein the hydrocarbon targeted for adsorption is a hydrocarbon having 2 to 5 carbon atoms.

12. The molded article for hydrocarbon adsorption according to claim 11, wherein the hydrocarbon having 2 to 5 carbon atoms is 1,3-butadiene.

13. The molded article for hydrocarbon adsorption according to claim 1, which is produced by a tableting method.

14. A method for producing a molded article for hydrocarbon adsorption, comprising annealing the molded article according to claim 1 obtained by tableting at a temperature equal to or higher than the glass transition temperature (Tg) of the polymer binder (B).

* * * * *